United States Patent
Adam

(10) Patent No.: US 6,461,360 B1
(45) Date of Patent: *Oct. 8, 2002

(54) LOCKING NAIL FOR THE REPAIR OF FEMUR SHAFT FRACTURES

(75) Inventor: Michael Adam, Heimberg (CH)

(73) Assignee: Sulzer Orthopedics Ltd., Baar (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/560,716

(22) Filed: Apr. 27, 2000

(30) Foreign Application Priority Data

May 12, 1999 (EP) .............................. 99810422

(51) Int. Cl.⁷ .............................. A61B 17/56
(52) U.S. Cl. .............................. 606/67; 606/62; 606/64
(58) Field of Search .............................. 606/64, 62, 63, 606/67, 68, 96, 98, 104

(56) References Cited

U.S. PATENT DOCUMENTS

| | | | | |
|---|---|---|---|---|
| 2,518,019 A | | 8/1950 | Kane | |
| 4,135,507 A | * | 1/1979 | Harris | 606/67 |
| 4,475,545 A | * | 10/1984 | Ender | 606/67 |
| 4,622,959 A | * | 11/1986 | Marcus | 606/67 |
| 5,374,235 A | * | 12/1994 | Ahrens | 606/62 |
| 5,697,930 A | * | 12/1997 | Itoman et al. | 606/62 |
| 5,713,902 A | * | 2/1998 | Friedl | 606/64 |
| 6,123,708 A | * | 9/2000 | Kilpela et al. | 606/62 |

FOREIGN PATENT DOCUMENTS

| | | |
|---|---|---|
| EP | 0355411 A1 | 2/1990 |
| EP | 0528128 A1 | 2/1993 |

* cited by examiner

*Primary Examiner*—Pedro Philogene
(74) *Attorney, Agent, or Firm*—Townsend and Townsend and Crew LLP

(57) ABSTRACT

The locking nail for the repair of femur shaft fractures, also in connection with trochanteric femur fractures, comprises a proximal nail section (2) and a distal nail section (3) adjoining the latter, with the nail sections (2, 3) having bores (2*e*, 2*f*, 2h, 2*i*, 3*a*, 3*b*, 3*c*) for the reception of bone screws, and with the distal nail section (3) having a curvature extending in an anterior-posterior plane (apE) and corresponding substantially to the antecurvature of the femur, with the proximal nail section (2) having at least over a partial section (2*a*, 2*b*) a continuous curvature, in particular with constant radius of curvature (R2), extending in a lateral-medial plane (lmE).

20 Claims, 2 Drawing Sheets

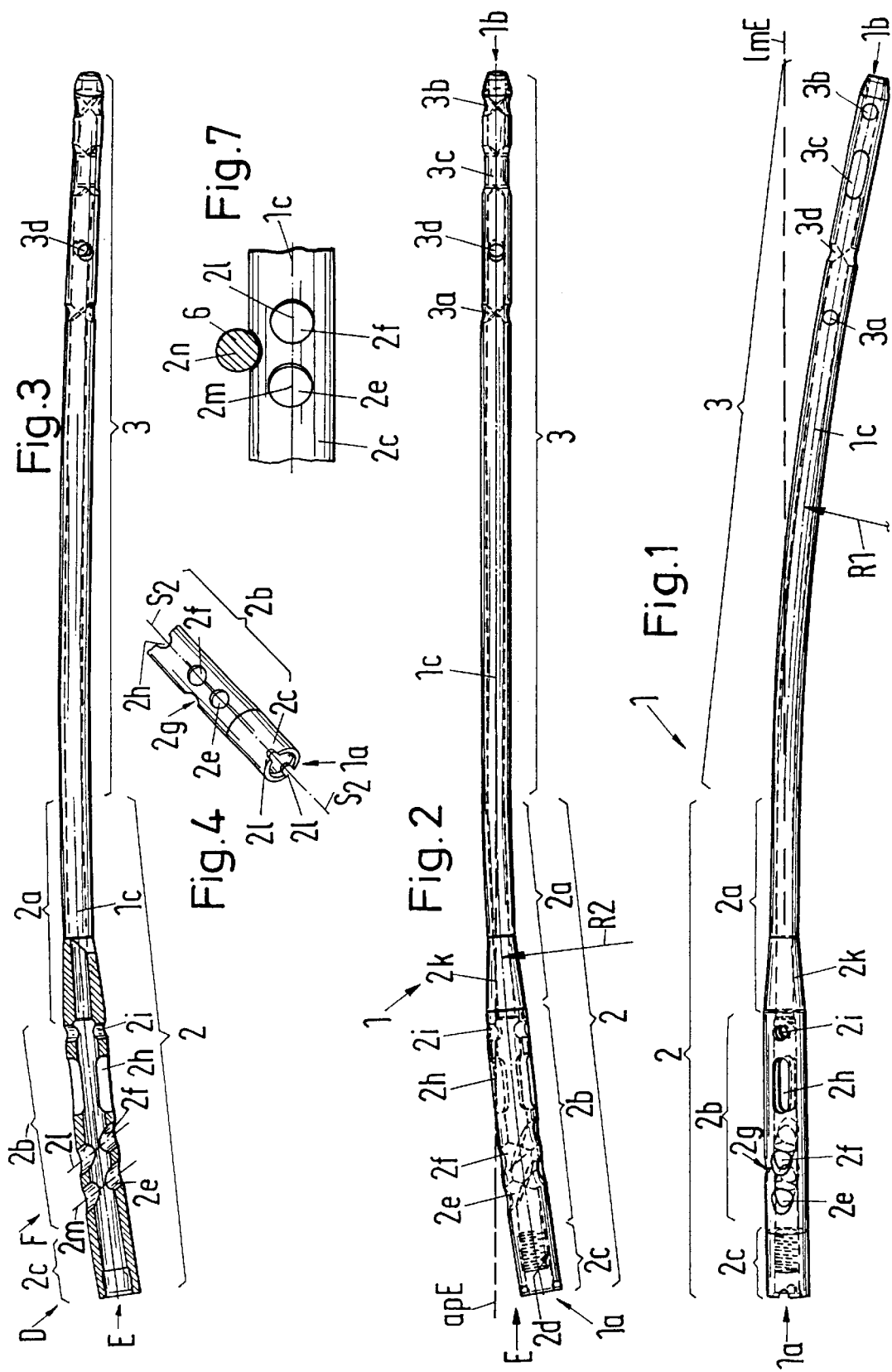

LOCKING NAIL FOR THE REPAIR OF FEMUR SHAFT FRACTURES

BACKGROUND OF THE INVENTION

1. Field of the Invention

The invention relates to a locking nail for the repair of femur shaft fracture and trochanteric femur fractures.

2. Description of the Prior Art

An osteosynthetic aid for the repair of intertrochanteric or subtrochanteric femur fractures which is designed as a locking nail with an open cloverleaf profile is known from the reference EP 0 528 128. The locking nail has inclined bores in its proximal section for guiding and holding a femoral neck screw. The locking nail has an axial longitudinal slit at its distal section. The locking nail also has a bend at the transition between a proximal partial section and a distal partial section. Disadvantageous in this known locking nail is the fact that it is difficult to introduce into the medullary space.

SUMMARY OF THE INVENTION

The object of the present invention is to create a more advantageous locking nail for the repair of femur shaft fractures.

This object is satisfied in particular by a locking nail comprising a proximal nail section and a distal nail section adjoining the latter, with these nail sections having bores for the reception of bone screws, and with the distal nail section having a curvature extending in an anterior-posterior plane and corresponding substantially to the antecurvature of the femur; and with the proximal nail section having at least over a partial section a continuous curvature, in particular with constant radius of curvature, extending in a lateral-medial plane. The term "continuous curvature" will be understood in the following to mean that the curvature has no point with a discontinuity or a bend respectively, which can be mathematically described in such a manner that the first derivative of the curvature plot has no discontinuity or no jump-like change.

In an advantageous embodiment the proximal nail section, starting from the distal nail section, has a transition section and a securing section adjoining the latter with bores for the reception of the bone screws, with the transition section and the securing section having a continuous curvature with a constant radius of curvature.

The locking nail in accordance with the invention is suitable in particular for the repair of femur shaft fractures, also in connection with trochanteric femur fractures, with the locking nail being manufactured with lengths of about 300 mm to 500 mm due to the inter-individually differing shaping of the femur. The locking nail is distinguished by a good mechanical hold in the medullary cavity and has a good rotational security. A transverse bore through which a bone screw is introduced in order to firmly hold the locking nail axially and in the direction of rotation is arranged in the lower distal nail section. The proximal nail section preferably has an inclined through-bore through which a femoral neck screw can be introduced.

The locking nail in accordance with the invention is preferably designed as a continuous hollow tube, in particular as a cylindrical hollow tube, and consists of a body-compatible, non-corroding material such as titanium or a titanium alloy. A guide wire is preferably introduced into the continuous hollow tube. The locking nail could however also be designed in the shape of a bar and have no hollow inner space extending in the axial direction.

An advantage of the locking nail in accordance with the invention is the fact that the latter can be introduced into the medullary space of the femur without a greater exertion of force even in an embodiment with low elasticity. The embodiment with low elasticity ensures a very good mechanical hold and a good support function in the medullary cavity.

The locking nail in accordance with the invention is designed in such a manner that the latter is preferably introduced into the femur or into its medullary space respectively starting from the trochanter major, with the introduction point being located slightly laterally with respect to the tip of the trochanter major. Since the trochanter major is arranged closer to the surface of the skin in comparison with the previously usual introduction location at the femur, the introduction via the trochanter major has the advantage that a smaller opening of the operation field is required, which in particular reduces the danger of infections. In addition the trochanter major is more easily accessible in the activities required during the operation. A locking nail was usually introduced into the medullary space in the region of the fossa piriformis. Blood vessels, etc. are also present at this location, however, so that the introduction via the trochanter major is more sure to avoid damage to these blood vessels. In an advantageous embodiment the locking nail has a securing section with a relatively small cross-section. This enables a locking nail to be formed with a smaller total cross-section, which has an advantageous effect on the introduction into the medullary space and in addition requires only a small opening of the operation field.

The locking nail which is known from the cited reference has at the transition location between the distal and the proximal nail section a bend location and is therefore difficult to introduce into the medullary space in spite of the elasticity produced by the longitudinal slit in the distal nail section since the medullary space has a curved extent and this nail lies in contact at certain locations at the medullary space wall or at the spongiosa and can be introduced into the medullary space only with a greater exertion of force. The locking nail in accordance with the invention with the curved proximal nail section has the advantage that the latter takes into account the anatomical shape of the medullary space in such an advantageous manner that it can be introduced without a greater exertion of force. In contrast to short locking nails, the locking nail in accordance with the invention, which is designed to be very long, must be rotated during the introduction into the medullary space by a partial rotation about its longitudinal axis. The locking nail in accordance with the invention has the property that the latter rotates into the correct final position by itself during the introduction into the medullary space since the outer shape of the locking nail is formed in imitation of the shape of the medullary space with respect to essential aspects. The locking nail which is known from the cited reference has a bend at the transition location between the proximal and distal nail section, which prevents a rotation of its own accord during the introduction into the medullary space. The locking nail which is known from the cited reference has the further disadvantage that the nail which is introduced into the medullary space is only rotatable to a limited extent since material protrudes into the longitudinal slit and forms an obstacle during the rotation. Since the locking nail in accordance with the invention does not necessarily require a longitudinal slit, it can also be manufactured more economically.

The locking nail in accordance with the invention can have a low elasticity and nevertheless be surely introduced without a greater exertion of force into the medullary space. Through the design of the locking nail in accordance with the invention a greater force, which is directed approximately radially outwardly and in particular weakens or destroys the femur corticalis, is avoided during its introduction into the medullary space. Through this it is also enabled that the femur is held together in its anatomically correct position. It is known that an unfavorably designed locking nail can cause the femur having the fracture to adapt to the shape of the locking nail, which has the result that the fixed femur has a faulty position or a deviation from the normal position respectively.

BRIEF DESCRIPTION OF THE DRAWINGS

FIG. 1 is a side view of the locking nail from the direction B;

FIG. 2 is a front view of the locking nail from the direction A;

FIG. 3 is a front view of the locking nail, which is rotated slightly about its axis, from the direction C, partly in section;

FIG. 4 is a detail view of the proximal nail section from the direction D;

FIG. 7 is a detail view of the securing section from the direction F.

DETAILED DESCRIPTION OF SPECIFIC EXEMPLARY EMBODIMENTS

Figure 5:
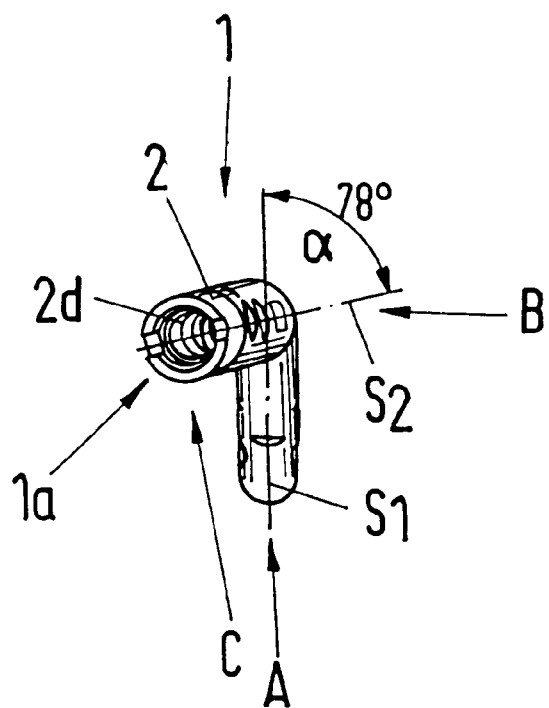
FIG. 5 is a detail view of the locking nail from the direction E.

The locking nail 1 in accordance with FIG. 1 is formed in a single piece and consists of a proximal nail section 2 and a distal nail section 3 adjoining at the latter. Starting from the proximal end 1a of the locking nail 1 the proximal nail section 2 comprises a thread section 2c extending in a straight line and having an inner thread 2d, adjoining thereat a securing section 2b which has a transverse bore 2i, an oval transverse bore 2h and two inclined bores 2e, 2f, and adjoining thereat a transition section 2a which extends conically contracting to the distal nail section 3. The surface of the securing section 2b has a groove 2g extending parallel to the inclined bores 2e, 2f. Depending on the fracture, bone screws can bores 2e, 2f and/or the groove 2g in order to secure the femur head. For this purpose an aiming device or a hammering-in tool is preferably used which is temporarily screwed into the inner thread 2d of the thread section 2c when the locking nail 1 is inserted into the femur in order to be able to screw in the bone screw with an exact guidance.

Adjoining at the transition section 2a the distal nail section 3 extends up to the distal nail end 1b. The center line 1c which extends in the middle of the locking nail 1 is illustrated between the proximal nail end 1a and the distal nail end 1b. The anterior-posterior plane apE extends corresponding to the plane of view in accordance with FIG. 1. The distal nail section 3 has a curvature which extends in this anterior-posterior plane apE and which is substantially designed corresponding to the antecurvature of the femur. The curvature of the distal nail section 3 or of its middle line 1c is preferably designed as a circular segment, with the radius of curvature R1 amounting to for example 2 meters depending on the anatomical form of the femur. Transverse bores 3a, 3b, 3d and an oval transverse bore 3c are placed in the distal nail section 3 for the reception of bone screws.

In FIG. 1 the lateral-medial plane lmE, which extends perpendicularly to the plane of view or to the anterior-posterior plane apE respectively, is also illustrated. The lateral-medial plane lmE extends corresponding to the plane of view in accordance with FIG. 2. In FIG. 2 the anterior-posterior plane apE, which extends perpendicularly to the plane of view or to the lateral-medial plane lmE, is also illustrated.

The front view of the locking nail 1 from the direction A in accordance with FIG. 2 shows the distal nail section 3, which extends in a straight line in the lateral-medial plane lmE from this point of view and at which the two, the transition section 2a and the securing section 2b, having a common curvature with a constant radius of curvature R2, adjoin. The following thread section 2c is designed in the illustrated exemplary embodiment to extend in a straight line, but could however also be designed to extend curvilinearly and in particular have the same radius of curvature R2. The partial section 2a, 2b or, respectively, the center line 1c which extends in the lateral-medial plane lmE, has a constant radius of curvature R2 and extends in the axial direction at least over about a fourth of the total length of the locking nail 1, and preferably over about a third of its total length.

The detail view illustrated in FIG. 4 from the direction D shows a part of the proximal nail section 2, namely the securing section 2b and the thread section 2c. In the securing section 2b the openings of the first and second inclined bore 2e, 2f, the notch 2g and a part of the oval transverse bore 2h can be seen. In addition the proximal nail section 2 has two notches 21 at the proximal nail end 1a. The notches 21, the inclined bores 2e, 2f and the oval transverse bore 2h all extend in the same plane S2. As can be seen in FIG. 3 the center lines 2m, 21 of the inclined bores 2e, 2f extend parallel to one another, with the notch 2g also extending parallel to the inclined bores 2e, 2f in FIG. 4. In further exemplary embodiments the inclined bores 2e, 2f could also extend not parallel to one another.

FIG. 7 shows a plan view from the direction F onto a segment of the securing section 2b with inclined bores 2e, 2f and notch 2g, with the direction F extending parallel to the center lines 2m, 21. A screw 6 with a center line 2n is arranged in the ventrally arranged notch 2g. In the illustrated exemplary embodiment the center lines 2m, 21, 2n are spaced to form an equilateral triangle, with the center lines 2m, 21 extending through the center line 1c of the locking nail 1. The distance between the center lines 21, 2n and the center lines 2m, 2n amounts for example to 8 mm. The proximal nail section 2 is firmly connected to the femur by one, two or three screws 6 which are arranged to pass through the two inclined bores 2e, 2f and the notch 2g. This arrangement of two inclined bores 2e, 2f and of the notch 2g has the advantage that the diameter of the proximal nail section 2 can be designed relatively thin and nevertheless a secure anchoring of the locking nail 1 by means of bone screws 6 is possible. The locking nail 1 can for example be designed in such a manner that the proximal nail section 2 has a diameter between 13 and 15 mm and the distal nail section 3 has a diameter between 9 and 13 mm. A locking nail 1 which is designed to be so thin has the advantage that it requires only a small opening of the operation field for its implantation. Thus a lower danger of infection is present during the implanting due to the small skin opening required. The securing section 2b with inclined bores 2e, 2f and ventrally arranged notch 2g, in particular in accordance with the embodiment illustrated in FIG. 4 and FIG. 7, could also be used separately from the other parts 2c, 2a and the distal nail section 3 in a differently designed locking nail. A securing section 2b of this kind could also be designed to extend in a straight line or curvilinearly respectively in the axial direction. FIG. 5 shows a front view of the proximal nail end 1a from the direction E. Starting from the proximal nail end 1a the locking nail 1 extends along the proximal nail section 2 in a left curve and extends after the transition to the distal nail section 3 in a downwardly pointing curve. A plane S1 extending in the direction of view perpendicularly through the distal nail section 3 and the plane S2 extending through the notches 21, the inclined bores 2e, 2f and the oval transverse bore 2h intersect at an angle of 78 degrees. The proximal nail section 2 thus has an anteversion of 78 degrees with respect to the distal nail section 1. This anteversion is required in order that the inclined bores 2e, 2f and the transverse bore 2h respectively extend in the direction of the femur neck or of the femur head respectively when the locking nail 1 is inserted in the femur. The anteversion amounts preferably to between 75 degrees and 80 degrees, depending on the anatomical form of the femur. The German term "Antetorsion" is called "anteversion" in English.

FIG. 3 shows the locking nail 1 from the direction of view C, which extends perpendicularly to the plane S2. Relative to the illustration in accordance with FIG. 2 from the direction of view A the locking nail 1 is illustrated in accordance with FIG. 3 to be rotated by 12 degrees about its longitudinal axis. The plane of intersection through the proximal nail section 2 corresponds to the plane S2 and extends parallel to the plane of view.

Figure 6:
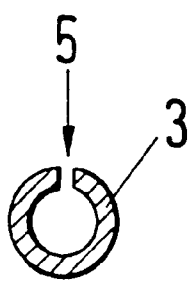
FIG. 6 is a cross-section through a slit locking nail.

FIG. 6 shows a section through a further exemplary embodiment of a distal nail section 3 having a gap 5 which extends in its longitudinal direction in order to lend a higher elasticity to the nail section 3. The locking nail 1 illustrated in FIGS. 1 to 5 is intended for a left femur. As a result of the physiological antecurvature and anteversion of the femur a right and left version of the locking nail 1 are required.

What is claimed is:

1. A locking nail for the repair of femur shaft fractures, also in connection with trochanteric femur fractures, the locking nail being adapted for the introduction into the medullary space of the femur starting from the trochanter major, the locking nail comprising a proximal nail section and a distal nail section adjoining the latter, with the nail sections having bores for the reception of bone screws, and with the distal nail section, before insertion into the femur, having a curvature extending in an anterior-posterior plane and corresponding substantially to the antecurvature of the femur, wherein the proximal nail section has at least over a partial section a continuous curvature with constant radius of curvature, extending in a lateral-medial plane, and wherein the proximal nail section includes at least one bore inclined such that a bone screw can be introduced through said bore into the femur neck.

2. A locking nail in accordance with claim 1, wherein the partial section having a continuous curvature in the axial direction extends at least over about one fourth of the total length of the locking nail.

3. A locking nail in accordance with claim 1, wherein the proximal nail section, starting from the distal nail section, consists of a transition section, a securing section adjoining the latter and a thread section adjoining the latter; in that the securing section contains bores; and in that at least the transition section and the securing section have a common curvature with a constant radius of curvature.

4. A locking nail in accordance with claim 3, wherein the thread section is designed to extend in a straight line and runs out to the proximal nail end, with the thread section having an inner thread for the reception of an aiming device or a tool for hammering in or out.

5. A locking nail in accordance with claim 3, wherein the transition section conically contractingly merges from the securing section to the distal nail section.

6. A locking nail in accordance with claim 1, wherein the locking nail is designed as a hollow tube.

7. A locking nail in accordance with claim 1, wherein the hollow tube has a slit extending in the axial direction in the distal nail section.

8. A locking nail in accordance with claim 1, wherein the partial section having a continuous curvature in the axial direction extends at least over about one third of the total length.

9. A locking nail in accordance with claim 1, wherein the bores are arranged to extend in the proximal nail section in such a manner that their axes have an anteversion of 75 degrees to 80 degrees relative to the distal nail section.

10. A locking nail for the repair of femur shaft fractures, also in connection with trochanteric femur fractures, comprising a proximal nail section and a distal nail section adjoining the latter, with the nail sections having bores for the reception of bone screws, and with the distal nail section having a curvature extending in an anterior-posterior plane and corresponding substantially to the antecurvature of the femur, wherein the proximal nail section has at least over a partial section a continuous curvature with constant radius of curvature, extending in a lateral-medial plane, wherein the proximal nail section has at least one inclined bore, wherein the proximal nail section has at its surface at least one notch which extends substantially parallel to the at least one inclined bore.

11. A locking nail in accordance with claim 10 wherein the notch is arranged to extend ventrally.

12. A locking nail in accordance with claim 10, wherein the inclined bores extend parallel to one another.

13. A locking nail in accordance with claim 10, wherein the proximal nail section has at its surface at least one notch which extends substantially parallel to the at least one inclined bore.

14. A locking nail in accordance with claim 13, wherein the notch is arranged to extend ventrally.

15. A locking nail in accordance with claim 10, wherein two inclined bores and a notch are arranged to extend parallel to one another and in particular to form an isosceles or equilateral triangle.

16. A locking nail for the repair of femur shaft fractures, also in connection with trochanteric femur fractures, comprising a proximal nail section and a distal nail section adjoining the latter, with the nail sections having bores for the reception of bone screws, and with the distal nail section having a curvature extending in an anterior-posterior plane and corresponding substantially to the antecurvature of the femur, wherein the proximal nail section has at least over a partial section a continuous curvature with constant radius of curvature, extending in a lateral-medial plane, wherein the proximal nail section has at least one inclined bore, wherein two inclined bores and a notch are arranged to extend parallel to one another and in particular to form an isosceles or equilateral triangle.

17. A locking nail for the repair of femur shaft fractures, also in connection with trochanteric femur fractures, comprising a proximal nail section and a distal nail section adjoining the latter, with the nail sections having bores for the reception of bone screws, and with the distal nail section having a curvature extending in an anterior-posterior plane and corresponding substantially to the antecurvature of the femur, wherein the proximal nail section has at least over a partial section a continuous curvature with constant radius of curvature, extending in a lateral-medial plane, wherein the bores are arranged to extend in the proximal nail section in such a manner that their axes have an anteversion of 75 degrees to 80 degrees relative to the distal nail section.

18. A locking nail for the repair of femur shaft fractures, also in connection with trochanteric femur fractures, comprising a proximal nail section and a distal nail section adjoining the latter, with the nail sections having bores for the reception of bone screws, and with the distal nail section having a curvature extending only in an anterior-posterior plane and corresponding substantially to the antecurvature of the femur, wherein the proximal nail section has at least over a partial section a continuous curvature with constant radius of curvature, extending in a lateral-medial plane.

19. A locking nail for the repair of femur shaft fractures, also in connection with trochanteric femur fractures, the locking nail comprising a proximal nail section and a distal nail section adjoining the latter, wherein each nail section has at least one oval transverse bore for the reception of bone screws.

20. The locking nail of claim 19 wherein the distal nail section, before the insertion into the femur, has a curvature extending in an anterior-posterior plane corresponding substantially to the antecurvature of the femur, and wherein the proximal nail section has at least over a partial section a continuous curvature with constant radius of curvature, extending in a lateral-medial plane.

* * * * *